United States Patent
Gustafsson et al.

(10) Patent No.: US 6,960,197 B1
(45) Date of Patent: Nov. 1, 2005

(54) ABSORBENT PANTS

(75) Inventors: Anders Gustafsson, Billdal (SE); Urban Widlund, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 08/875,246

(22) PCT Filed: Feb. 1, 1996

(86) PCT No.: PCT/SE96/00118

§ 371 (c)(1),
(2), (4) Date: Aug. 14, 1997

(87) PCT Pub. No.: WO96/23466

PCT Pub. Date: Aug. 8, 1996

(30) Foreign Application Priority Data

Feb. 2, 1995 (SE) .................................... 9500386

(51) Int. Cl.[7] .......................... A61F 13/15; A61F 13/20
(52) U.S. Cl. ..................... 604/348; 604/354; 604/355; 604/385.19; 604/385.23; 604/385.29; 604/396
(58) Field of Search .................... 604/385.1, 385.2, 604/393–402, 347–349, 354–355, 385.09, 604/385.14, 385.19, 392; 2/400–404; 602/67.73

(56) References Cited

U.S. PATENT DOCUMENTS

| | | | |
|---|---|---|---|
| 19,418 A | * 2/1858 | Hall | ......................... 604/392.2 |
| 1,695,109 A | 12/1928 | Kosloff | |
| 1,833,960 A | * 12/1931 | Alsop | ......................... 604/395 |
| 2,004,088 A | * 6/1935 | Alsop | ......................... 604/401 |
| 2,069,092 A | * 1/1937 | Jackson, Jr | .................. 604/397 |
| 2,102,359 A | * 12/1937 | Frieman | ...................... 604/396 |
| 2,450,789 A | * 10/1948 | Frieman | ...................... 604/401 |
| 2,468,445 A | * 4/1949 | Hurst | ....................... 604/397.2 |
| 2,538,758 A | * 1/1951 | Bricmont | ................. 604/347.2 |
| 2,837,095 A | * 6/1958 | Stevenson | .................... 604/395 |
| 3,532,093 A | * 10/1970 | Lovret | ...................... 604/348.2 |
| 3,769,978 A | * 11/1973 | DeNight et al. | ............. 604/374 |
| 3,860,003 A | 1/1975 | Buell | |
| 4,205,679 A | * 6/1980 | Repke et al. | ............... 604/394 |
| 4,421,512 A | 12/1983 | Papajohn | |
| 4,662,877 A | 5/1987 | Williams | |

(Continued)

FOREIGN PATENT DOCUMENTS

CA      672921     * 10/1963     .................. 604/395

(Continued)

OTHER PUBLICATIONS

Translation of Spanish Patent 2,022,026, Apr. 17, 1998.*

*Primary Examiner*—Karin Reichle
(74) *Attorney, Agent, or Firm*—Burns, Doane, Swecker & Mathis, L.L.P.

(57) ABSTRACT

Absorbent pants having a waist opening, two leg openings, and a waterproof outer barrier layer, which is arranged outside the pants layer. The pants layer has a surface area which is greater than that of the outer barrier layer and is joined in parts with itself or includes a device for enabling it to be joined in parts with itself, so that during use of the pants it alone constitutes the waist opening and the leg openings of the pants, and that the load-bearing parts of the pants and all of the parts lying against the body of the user are formed only from the pants layer. The pants are also elastic, where the outer barrier layer is essentially inelastic.

25 Claims, 7 Drawing Sheets

U.S. PATENT DOCUMENTS

| | | | |
|---|---|---|---|
| 4,756,709 A | | 7/1988 | Stevens |
| 5,325,543 A | * | 7/1994 | Allen .................. 604/385.142 |
| 5,407,438 A | * | 4/1995 | Hedlund et al. ....... 604/385.26 |
| 5,792,130 A | * | 8/1998 | Widlund et al. |
| 5,797,895 A | * | 8/1998 | Widlund et al. ...... 604/355.242 |
| 5,817,086 A | * | 10/1998 | Kling .................. 604/385.192 |
| 5,830,203 A | * | 11/1998 | Suzuki et al. ............ 604/385.2 |
| 5,928,211 A | * | 7/1999 | Gustafsson et al. |
| 6,120,485 A | * | 9/2000 | Gustafsson et al. ...... 604/397.2 |
| 6,132,409 A | * | 10/2000 | Vogt et al. ............ 604/385.192 |
| 6,152,907 A | * | 11/2000 | Widlund et al. ...... 604/385.192 |
| 6,152,908 A | * | 11/2000 | Widlund et al. ...... 604/385.192 |
| 6,156,951 A | * | 12/2000 | Gustafsson .......... 604/385.172 |
| 6,183,458 B1 | * | 2/2001 | Ahlstrand et al. .... 604/385.192 |

FOREIGN PATENT DOCUMENTS

| | | | | |
|---|---|---|---|---|
| CA | 1074501 | * | 4/1980 | ................ 604/396 |
| DE | 1240482 | * | 5/1967 | ................ 604/401 |
| DE | 2553017 | * | 6/1977 | ................ 604/347 |
| EP | 0 119 143 | | 9/1984 | |
| EP | 0 214 636 | | 3/1987 | |
| EP | 0 219 326 | | 4/1987 | |
| EP | 0 320 991 | | 6/1989 | |
| EP | 0 359 410 | | 3/1990 | |
| EP | 0 581 044 | | 2/1994 | |
| EP | 0626160 | * | 11/1994 | ............. 604/385.2 |
| ES | 2022026 | * | 11/1991 | |
| FR | 1264984 | * | 5/1961 | ................ 604/397 |
| FR | 1501868 | * | 11/1967 | ................ 604/398 |
| GB | 1411087 | | 10/1975 | |
| GB | 2042342 | * | 9/1980 | ............. 604/385.1 |
| GB | 2 218 322 | | 11/1989 | |
| TW | 198226 | | 1/1993 | |
| WO | 1 411 087 | * | 10/1978 | ................ 604/396 |
| WO | 88/07337 | | 10/1988 | |
| WO | 93/09746 | | 5/1993 | |
| WO | 93/17648 | | 9/1993 | |
| WO | 94/28844 | | 12/1994 | |
| WO | 95/16418 | | 6/1995 | |
| WO | 95 16418 | * | 6/1995 | |
| WO | 96 23464 | * | 8/1996 | |
| WO | 96 23465 | * | 8/1996 | |
| WO | WO 9848753 A1 | * | 11/1998 | ........... A61F 13/15 |

* cited by examiner

ABSORBENT PANTS

BACKGROUND OF THE INVENTION

The present invention relates to an absorbent pants which have a waist opening and two leg openings, said pants include a pants layer, which during use of the pants is intended to be turned toward the body of the user, and an outer barrier layer, which is liquid-tight and placed outside the pants layer facing away from the body of the user during use of the pants.

Absorbent products in the form of diapers have been known for a long time, both for single-use and re-use. A fundamental task for such products is to be able to collect and store body fluids excreted by the user, i.e. urine and faeces. In this connection it is important to see to it that the product is so constructed that urine and faeces first and foremost can be introduced into the product in a secure manner, i.e. that liquid and faeces do not already miss their target during the moment of excretion and end instead up to one side of the intended acquisition area. It is further at least equally important to make sure that fluids and faeces which find the right acquisition area later cannot leak out from their storage regions.

Alongside these main tasks for diapers, there are also other important demands put upon them, for example they should fit comfortably and pliably at the right place on the user, they should not cause any skin irritation to the user and they should not be made of substances which can harm our environment.

In many respects the different demands from the user work together in the endeavour to construct as good a diaper as possible. For example, the fit of the diaper and its fastening system influence the diaper's ability to quickly and securely receive urine and faeces without any leakage arising. Most of today's disposable diapers are therefore equipped with some sort of elastic leg cuffs, with the intention that these should tightly close around the leg of the user, and in this way prevent leakage. A known example of such a diaper is described in U.S. Pat. No. 3,860,003. The diaper has leg cuffs or side flaps outside the absorption body, which have pretensioned elastic bands applied to them. The intention is that the elastic bands shall contract the side flaps and in this manner form an elastically contractable contact line between the leg cuff of the diaper and the skin of the user. However, there is still a very large risk for leakage because there is only a relatively narrow contact line which is supposed to prevent the fluid which is not immediately absorbed by the absorption body from running out over the edges of the diaper. The pressure on this narrow line can be rather high and the fluid, does not have a very large distance to travel before it passes the contact line once the contact is no longer sufficient to withstand leakage. Furthermore, a large tensioning of the elastic band is required to ensure that the leg cuff does not lose contact with the skin of the user. This can in turn lead to a problem, namely chafing of the skin. Even if the leg cuffs would be able to resist the pressure from the fluid and not let it pass by, the fluid would instead accumulate above the absorption body and cause the skin to be moist, which in itself can lead to skin irritations.

With the aim of increasing the security against leakage, especially of loose faeces, past the side flaps or leg cuffs of the diaper, many of today's diapers are equipped with extra barrier flaps inside the elastic leg cuffs. An example of such a diaper is shown in EP 0 219 326. This patent has an object, among others, to achieve a diaper with double leakage protection and to create a channel with the help of the raised barrier flap, which would be able to retain body fluids in the diaper. The barrier flap is raised, among other places, along the inner part of the thigh of the user in the crotch region.

Body fluids which are not immediately absorbed by the absorption body in the diaper, for example loose faeces, are stopped by the barrier flap and are collected in the said channel. If body fluids nevertheless should manage to run past the barrier flaps, it is stated that the leg cuffs (the gasketing cuff) will form a further barrier against leakage. Even if the diaper according to EP 0 219 326 is equipped with a further barrier inside that already known, it still has the same disadvantage as the latter, i.e. that there is only a narrow line of contact against the skin of the user. This narrow line of contact can easily lose contact with the skin of the user when the barrier is subjected to a large pressure from, for example, a large quantity of urine. It has obviously been considered that the barrier flap will not be sufficiently resistent to prevent fluid from escaping over the barrier, as the precaution has been taken to have the elastic leg cuffs outside the barrier flaps. In the same way as for the known elastic leg cuffs, this still leaves a large area (even if it is a smaller area than earlier) of the skin of the user open to exposure to the fluid or faeces which collect in the so-called channel between the barrier flap and the absorption body, i.e. the risk for skin irritation is evident. This barrier construction is therefore far from being perfect.

It must be observed that there are also diapers on the market like the diaper described in the patent, which are equipped with a similar leakage barrier around the waist opening part of the diaper. The problem with leakage is therefore not only limited to the leg openings of the diaper.

Recently, a new type of diaper has been produced and launched on the market, the so-called pants diaper. These differ from the traditional diapers first of all with respect to the fastening system, i.e. the system which makes the pants diaper, respectively the normal or "open" diaper, stay in place on the user. Open diapers are sealed to form a pants on the user by means of fastening means of various types, for example adhesive tape ribbons, hook and loop fasteners or press studs. Pants diapers are, on the other hand, sealed at the edges already during manufacture so as to form a pants which has a waist opening and two leg openings. The sealing of the side seam in the respective side parts can be made in many ways, for example by means of a straight glue joint or a welded seam. The pants cover of the pants diaper can also be included as part of the fastening system of pants diaper. By this, it is meant that the cover because of its elastic capacity holds the pants diaper tightly around the body of the user and prevents the pants diaper from slipping down on the user. Naturally, there are other factors which influence the ability of the pants diapers to stay put at the intended place on the user. The difference between pants diapers and open diapers lies in that the latter can be tightened around the waist of the user by means of the fastening means, in the same way one can tighten a waist belt on a pair of long pants. Pants diapers are, however, not equipped with such tightenable fastening means, but must normally rely on their elastically tight covering.

There are many known pants diapers, for example those shown in EP 0 320 991. This pants diaper has a central absorption unit and two elastic side panels which are joined with the side edges of the absorption unit. Together they form a waist opening and two leg openings. The pants diaper is, in a way which is known for open diapers, furthermore equipped with elastic means along parts of the leg openings and the waist opening. The absorption unit comprises an absorption body between a liquid-permeable inner covering layer and a liquid-impermeable outer covering layer. The space between the inner covering layer and the skin of the user will be extremely limited, and consequently faeces which are deposited on the inner covering layer are liable to be in contact with the skin of the user and to be smeared over it. The inner covering layer will also become wet from the urine given off by the user. It is obviously not desirable that the skin of the user shall be in contact with a moist covering layer, which will be the case in the parts of the inner covering layer which at least occasionally come into contact with the skin of the user.

A characteristic for known pants diapers (and also for known open diapers) is that it is the outer covering layer, i.e. that which is applied outside the absorption body, which forms the load-bearing covering layer of the pants. This load-bearing covering layer is defined as the covering which one is left with, if one takes away all layers and elements comprised in the pants which do not actively contribute to form a waist opening and two leg openings of a pants, and without which the pants would no longer be able to be held together around the body of a user. Especially important load-bearing parts are the so-called side seams, i.e. the parts of the pants in which the front and rear parts of the pants-forming layer are joined in order to form the waist opening and the leg openings.

The load-bearing pants-forming covering layer for the known pants diaper according to EP 0 320 991 is formed of the two elastic side panels. The outer covering layer is applied outside the absorption body. In this case, the load-bearing pants-forming covering layer is made up of several pieces of material joined together. When the absorption body is filled with urine, the weight of the absorption body presses against the outer covering layer applied outside the absorption body, subjecting it to an increasing gravitational force, which in turn is transferred to the elastic side panels and the inner covering layer to which the outer covering layer is joined. This leads to the elastic side panels being stretched out and to the distance between the user and the inner covering layer increasing, thus, increasing the risk of leakage.

Another example of a pants diaper in which the outer covering layer forms the load-bearing pants-forming layer is WO 88/07337. In this case the outer covering layer is elastic. The absorption body is applied inside the elastic pants-forming covering layer as reckoned towards the body of the user.

In an attempt to improve the gripping and mounting characteristics of a pants diaper, it has been suggested in WO 93/17648 to equip a pants diaper with an elastically stretchable region in the front and/or rear parts of the pants diaper, while the crotch part is comparatively unstretchable. This pants diaper is however still traditionally constructed, in so far as the outer covering layer of the pants diaper forms the pants-forming layer of the pants diaper and that the absorption body in this way is arranged inside this pants-forming layer.

It has further been suggested to equip open diapers with a covering layer facing towards the user with one or more openings for the passage of urine and/or faeces down to a sort of pocket with an absorption body as the bottom of the pocket, in order in this way to isolate the skin of the user from contact with above all faeces. In U.S. Pat. No. 4,662,877 such a diaper is shown which comprises an upper layer, directed towards the body of the user and equipped with an elongated opening. Elastic bands are arranged along the edges of the opening with the intention of forcing the edges of the opening up from the absorption body lying below. Other elastic arrangements are also conceivable according to this patent.

EP 0 359 410 describes a similar diaper which has an elastic covering layer, equipped with an opening, which faces the body. An empty space is formed between the covering layer and the absorption core.

By analogy with the pants diaper above, it is noticeable that even if the covering layer of the diaper facing towards the user gives more liberty than that which has been the case for earlier known diapers with covering layers facing towards the body, it is still the outer covering layer of the diaper, i.e. the layer which is applied outside the absorption core as seen from the user, which is the layer that supports the diaper during use of same, i.e. after the diaper has been taped together with the fastening tapes on the user. The load-bearing outer covering layer is also at a distance from the body of the user, which leads to a large uncertainty concerning the position of the possible leakage barriers in relation to or contact with the genitals respectively anus of the user.

Finally, it is also known from U.S. Pat. No. 4,756,709 to arrange elastic zones with mutually different elastic directions of force in a pants-forming outer covering. In rear and front waist parts of the covering the covering is stretchable in the cross direction and in the intermediate crotch part it is stretchable in the longitudinal direction. This pants-forming covering layer, like those enumerated above, is arranged outside the absorption body.

OBJECTS AND SUMMARY

An object of the present invention is to solve the problem that excreted fluids, which are not immediately absorbed by the absorption body, risk leaking out over some edges of the product.

Another object of the present invention is to prevent or at least obstruct faeces and urine received in the pants from coming into contact with the skin of the user.

A further object of the present invention is to solve the problem of ensuring that emitted urine and faeces are directly collected in the collection regions arranged for this purpose in the pants.

Yet another object of the present invention is to solve the problem of preventing the covering layer facing towards the body of the user being moved out of its position in relation to the user.

This is brought about by an absorbent pants of the type mentioned in the introduction which is characterized in that the pants layer has a surface which is greater than the outer barrier layer, that the pants surface is joined in parts with itself or comprises means to enable it to be joined in parts with itself, so that during use of the pants it alone constitutes the waist opening and leg openings of the pants and that load-bearing parts of the pants and all the parts in contact with the body of the user are in this way built up from only the pants layer.

According to one aspect of the invention, an absorbent pants comprises a hydrophobic pants layer which during use of the pants faces a body of a user, the pants layer being assembled to itself or being able to be assembled to itself so that the pants layer by itself defines a waist opening and two leg openings. The absorbent pants are arranged such that only the pants layer of the absorbent pants are in contact with the user when the absorbent pants are being worn. The absorbent pants includes an outer barrier layer which is impermeable and arranged outside of the pants layer relative to the body of the user during use of the pants and is fastened to the pants layer, the pants layer has a surface area which is greater than a surface area of the outer barrier layer. The absorbent pants further includes at least one absorption body arranged between the pants layer and the outer barrier layer, and a liquid-permeable covering layer arranged on the absorption body between the absorption body and the pants layer, the absorption body being arranged between the liquid-permeable covering layer and the outer barrier layer. The liquid-permeable covering layer extends laterally beyond the absorption body and portions of the liquid-permeable covering layer that extend laterally beyond the absorption body and is affixed to the outer barrier layer to laterally surround the absorption body. The pants layer, the outer barrier layer, and the liquid-permeable covering layer are arranged so as to define a space in the form of a pocket between the pants layer and the liquid-permeable covering layer. Further, at least one opening in the pants layer is arranged over the pocket for passage of at least one of urine and faeces into the pocket.

According to a further aspect of the invention this is achieved by an absorbent article, such as a diaper, an incontinence protection or a sanitary napkin, which is characterized by an inner pants, which in its entirety during use fits in contact directly against the skin and genitals of the user, as well as an absorption unit, which is applied on the outside of the inner pants and is supported by it.

The expression "inner pants" means the same thing as the expression "pants layer" which is used in the description and other claims. The expression "absorption unit" means a unit which is intended to take up and retain urine and/or faeces or in appropriate case menstruation fluids.

By turning around the ingrained thought that the load-bearing pants-forming covering layer shall always be arranged outermost as seen from the user and also that this layer should be arranged outside the absorption body, an absorbent pants has now been achieved which fits tightly against the body of the user and in which the outer covering layer or barrier layer and the absorption material are liberated from the influences or forces from the pants layer. In former diapers and pants diapers, the outer covering layer has been left to support the biggest part of the forces which work to hold the diaper in place around the waist of the user. In an attempt to achieve contact between the leakage-proof outer barrier layer, different barriers have been built up from this outer layer, which in the best case would achieve one or several narrow contact lines with the user.

The present invention has instead a completely turned-around construction. It is the covering layer facing towards the body of the user which instead forms the pants and which takes up all the forces which work together to hold the pants in place around the waist of the user. The absorption material comprised in the pants, e.g. placed in an absorption body, and the outer barrier layer, are disengaged from all the pants-forming and load-bearing parts of the pants and instead constitute a load on the outside of the pants-forming layer in contact with the body. The pants-forming pants layer can be likened to a second skin which is pulled over the skin of the user. The outer barrier layer can be likened to a collection container, a pocket or a bag, which is fastened to the "second skin". This collection container does not in itself contribute to forming the pants. The possibly present absorption body is preferably arranged in this collection container or pocket.

In an advantageous embodiment of the invention, the elastic means are pretensioned and applied in the transverse direction in the front respectively the rear waist parts of the pants layer and applied pretensioned in the longitudinal direction in the crotch part of the pants layer, whereby the front respectively the rear waist parts have elastic forces which principally work in the circumferential direction of the pants waist opening, and the crotch part has elastic forces which work primarily in the circumferential direction of the pants leg openings.

In a further advantageous embodiment of the invention, the outer barrier layer has end and side edges, of which the side edges are joined with the pants layer in the region between the respective side seams and the intended longitudinal line of symmetry, so that the outer barrier layer is essentially unstressed by tensile forces perpendicular to the longitudinal line of symmetry between these joining regions and the joining region for the ends of the outer barrier and the pants layer.

According to an especially advantageous embodiment of the invention, the pants layer is hydrophobic and has at least one opening for the passage of urine and/or faeces.

In another especially advantageous embodiment of the invention, the outer barrier layer is arranged at the level of the opening or openings, and the outer barrier layer is joined with the pants layer in the region around the opening or openings.

In a further especially advantageous embodiment of the invention, the pants layer has at least one opening arranged inside a front part of the crotch region seen in a direction towards the front waist part, and at least one opening arranged in a rear region of the crotch part, seen in the direction towards the rear waist opening, intended for the passage of urine respectively faeces through the pants layer to a front respectively a rear pocket between the pants layer and the outer barrier layer, these pockets are separated from each other so that transportation of urine respectively faeces between the pockets is prevented.

Thanks to the pants layer according to the invention being pliably placed on the body of the user, it is now possible in a reliable way to place the opening or openings in the regions of the pants layer which are intended to be in contact with the genitals respectively anus of the intended pants user, with the assurance that the opening or openings during use of the pants will not later move away so that the opening or openings end up in the wrong place. Consequently, the openings do not have to be made bigger than necessary, whereby it is not necessary to expose larger areas of the genitals, anus or surrounding skin parts of the user, than necessary. This contributes to that the skin of the user can be held as clean and dry as possible. As above all the accuracy of aim is increased, i.e. the assurance that urine respectively faeces reach the opening or respective opening, the pants layer will be held very dry and because of this, the skin of the user will also be held dryer than with earlier known diapers and pants diaper.

Yet another advantage with being able to store faeces well enclosed in a pocket is that faeces, especially hard faeces, cannot spill out onto for example a changing table during changing of the pants diaper. Especially for earlier known elastic pants diaper the problem has occurred that tearing open of the first of the two side seams causes the pants diaper to quickly contract. If the pants diaper contain hard faeces lying loosely on the inner covering layer, there is a large risk that the faeces spill out and end up on the changing table, or on another surface adjacent the place where changing is taking place. According to the present advantageous embodiment of the invention, the faeces will be well enclosed in their pocket between the pants layer and the outer barrier layer, and spilling of faeces is prevented.

Further advantages and features of the invention can be seen in the following claims and the following description of the embodiment.

DESCRIPTION OF THE DRAWINGS

The invention shall now be described in detail with reference to the embodiments shown in the drawings, in which.

DESCRIPTION OF THE EMBODIMENTS

In the descriptions of the different embodiments, the same reference numerals will be used again for such details and structural elements which are the same for the embodiments in the different Figures.

Figure 1:
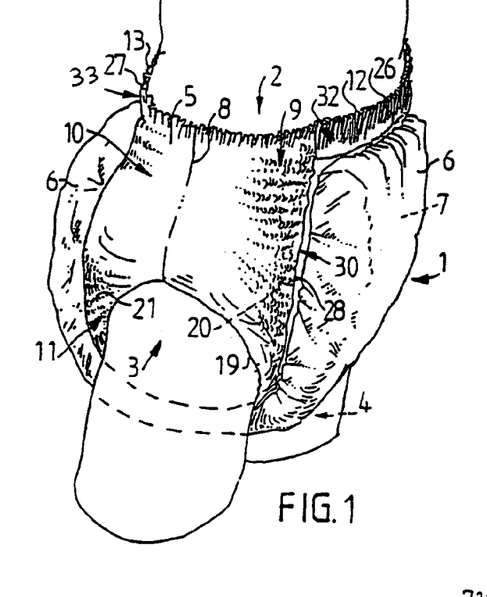
FIG. 1 shows a perspective view from the side of an absorbent pants according to a first embodiment of the invention, as shown on a schematically indicated user.

FIG. 1 shows absorbent pants 1 according to the invention, as it is intended to be used on a user. The user is schematically indicated in FIG. 1 in the form of truncated waist and leg parts. The pants has a waist opening 2 and two leg openings 3 and 4, one of these however being obscured in FIG. 1.

The pants comprises a pants layer 5, an outer barrier layer 6 and an absorption body 7 arranged between these.

Figure 3:
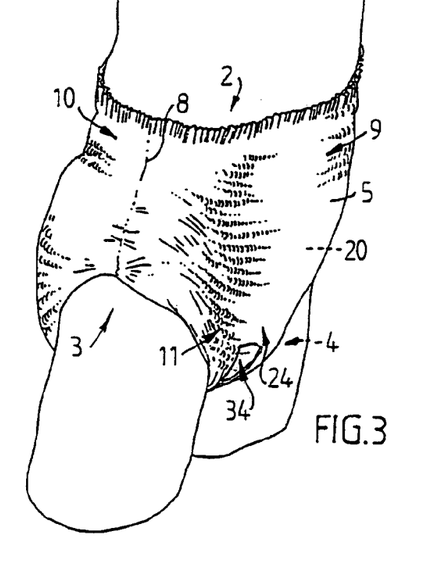
FIG. 3 shows in the same way a perspective view from the side of the load-bearing pants layer of an absorbent pants according to the first or the second embodiment of the invention (FIG. 1 respectively 2) and with other details of the pants removed.

Pants layer 5 is facing towards the body of the user and is in contact therewith over essentially all its area, which is best shown in FIG. 3. In this Figure the absorption body and the outer barrier layer have been removed for the sake of clarity. The pants layer 5 can be seen to tightly fit around the body of the user. FIG. 3 also shows that the pants layer forms a pants configuration in itself forming the pants waist opening 2 and leg openings 3 and 4. Further layers or parts are not necessary in order to achieve self-supporting pants.

Pants layer 5 is joined at its side parts with two side seams, one on each side, whereby only the one 8 is shown in FIGS. 1 and 3. The side seams extend from the waist opening 2 to the respective leg openings 3,4. The side seams can for example be made of a continuous or discontinuous glue joint or welded joint. The latter can for example be achieved by means of ultrasonic welding. It is, however, not necessary that the side seams are made of a joint of this type made by the diaper manufacturer. The side parts of the pants layer can instead be equipped with fastening means, which either are openable and reclosable or which are intended to be joined together by the user from an unjoined position to a joined position in a way decided in advance by the diaper manufacturer, so that a diaper is formed. Such pants look like and act during use substantially in the same way as a pants which has side seams formed by glued or welded joints. Examples of absorbent pants with such alternative side seams can be seen in our Swedish patent applications SE 9401224-2, SE 9401225-9, SE 9401226-7, SE 9401227-5, SE 9401228-3.

Figure 7:
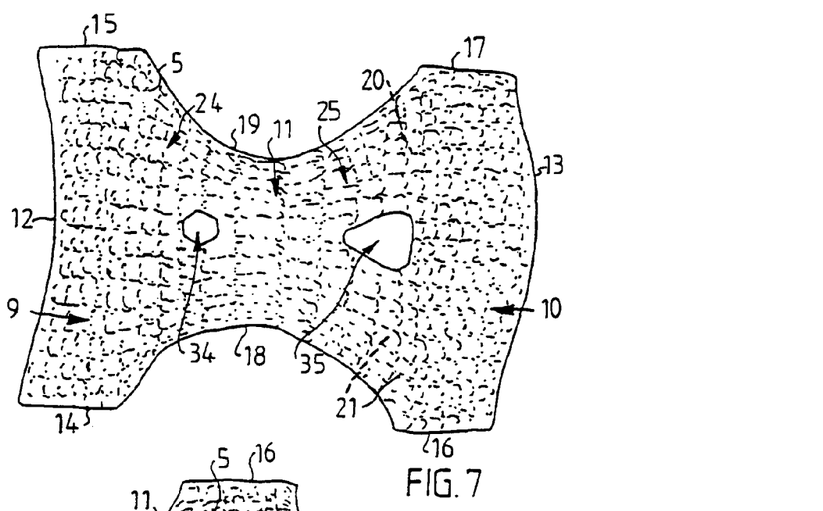
FIG. 7 shows schematically a plan view of a pants layer in the stretched condition according to the first or the second embodiment of the invention, seen from the side in contact with the user.

With reference to FIG. 7, an example is shown of a pants layer 5 as it appears before it is joined together to the pants configuration such as in FIG. 1. Pants layer 5 comprises a front and a rear waist part 9 and 10. These waist parts 9,10 together surround the stomach respectively backside of the user, see FIGS. 1 and 3. Pants layer 5 also comprises a crotch part 11 between the two waist parts 9,10. The crotch part is placed between the legs of the user during use of the pants. There is, however, no fixed border for the transition from the waist parts 9,10 to the crotch part 11. The waist parts 9,10 do not need to have the same width, but can have different widths, e.g. the back waist part could be wider than the front.

Both waist parts 9,10 each have an end edge 12 respectively 13 and two side edges 14,15 respectively 16,17. The crotch part has two side edges 18,19. The side edges 14,16 respectively 15,17 of the respective front and rear waist parts on the same side of an imaginary longitudinal line of symmetry drawn from the end edge 12 of the front waist part 9 to end edge 13 of the rear waist part 10, are joined to each other to form the side seams, of which, as mentioned above, only one side seam 8 (which joins together side edges 15,17) is shown in FIGS. 1 and 3. Side seam 8 is shown only schematically in FIGS. 1 and 3. The man skilled in the art knows that there are many ways to join side edges 14,16 respectively 15,17 to each other. For example, the side edges can overlap or they can be joined to the same side of the pants layer facing towards each other. In the last case the side seams can either face away from the user or face in towards the user.

Figure 6:
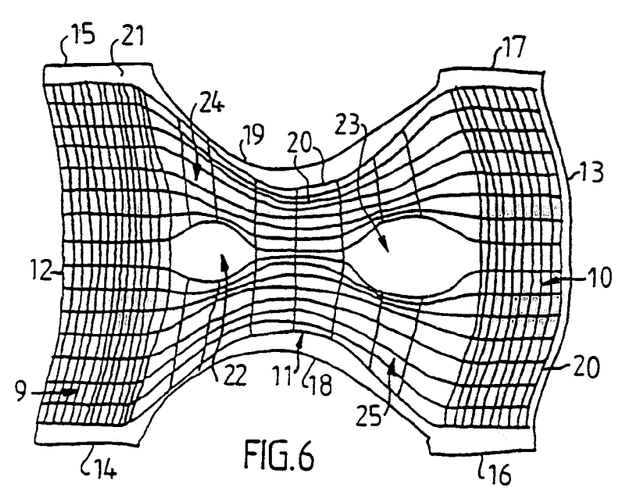
FIG. 6 shows schematically a plan view of an elastic means in the stretched condition applied to a material layer in a pants layer according to the first embodiment of the invention.

Pants layer 5 is elastic. With reference to FIGS. 1, 6 and 7, an example is shown of an elastic pants layer, which comprises an elastic means 20 and at least one essentially in-elastic material layer 21. The elastic means 20 are applied pretensioned onto the essentially inelastic material layer 21.

Elastic means 20 is shown in FIG. 6 as an elastic net, but an elastic film, an elastic tissue (nonwoven) or several elastic threads, ribbons or similar could also be used, whereby the latter in such a case are laid out over a large part of the material layer surface so that they together can be considered as a single elastic means.

The elastic means should have an elasticity in such a high degree that it can be stretched out to an extension of at least 25% of its unstretched, relaxed length, in other words to a length which is at least 1.25 times its unstretched length, and then, when released from the stretching force, should return to an extension of at most 15% of its original unstretched length. Preferably, the elastic means should be able to be stretched out much more than 25% of its relaxed length and should be able to return to its original relaxed length or almost back to it. This does not exclude that an elastic material which displays a yield point at which its extension and contraction characteristics change cannot be used, as long as it still displays elastic characteristics as above when past its yield point.

Elastic means 20 is elastic in both the longitudinal and transverse directions, or can be orientated in both longitudinal and transverse directions in the case it is made of threads or ribbon-shaped elements. The need for elasticity can be placed on both the longitudinal and transverse directions of the elastic means.

An example of a preferred elastic means is elastic net, which comprises components of thermoplastic A–B–A block copolymers. End block A can be a relatively stiff polymer, such as polystyrene or a polystyrene homolog. Middle block B can be a soft flexible polymer chain, such as polybutadiene, polyisoprene or poly(ethene-cobutene). These copolymers are often called SBS respectively SIS and are commercially available under the trademark KRATON G, respectively SEBS which is commercially available under the trademark KRATON D.

In order to improve the processibility of these materials, they are often blended with one or more polyolefines, e.g. polyethylene, polypropylene, polybutene, ethene copolymers, propene copolymers or butene copolymers.

The essentially inelastic material layer 21 can be formed from a fiber cloth (nonwoven), e.g. of meltblown, spunbond or thermobond type, e.g. comprising polypropene fibers. Thermoplastic films could also be used. The essentially elastic material layer should best be air- and vapour-permeable, as it will be in contact with the skin of the user and therefore should not be so airtight that the skin cannot breathe. By "essentially inelastic" in this connection is meant that the elasticity of the material layer is considerably less than the elasticity which is defined above for the elastic means 20. Material layer 21 can also be made of several pieces of material joined together, which in such a case together form the material layer 21 shown in FIGS. 6 and 7. In this connection it is worth pointing out that the shape of the pants layer is not limited to that shown in the Figures (an hourglass shape), but can be made differently if that would be appropriate, for example to dimension the pants for another size of user. Pants layer 5 shown in the Figures is suitable for children weighing between 10 to 15 kilograms. It is naturally also conceivable to have sizes for smaller or larger children, as well as sizes which will fit incontinent adult users.

With the intention of achieving preferred elastic lines of force in pants 1 and at the same time giving pants layer 5 a pants-like shape, the elastic net 20 is prestressed and placed in the transverse direction in the front respectively the rear waist parts 9,10 of the pants layer 5, and prestressed in the longitudinal direction in the crotch part 11 of pants layer 5. In order to achieve bent parts of the elastic net 20 which will closely follow the contours of the side edges 18,19, certain threads in the elastic net have been cut, abraded or broken by some other means. In this way, large apertures 22,23 are made in the net in a front 24 respectively a rear 25 part of the crotch part 11. It can be observed that even before breaking of certain threads in the elastic net 20, bent parts of the elastic net 20 could be obtained in the crotch part 11 of the pants layer. The bending is caused by the acting together of the transverse and longitudinal forces which are obtained when the net is stressed in the above mentioned way. It is, however, preferred that the net is configured, for example in the way shown in FIG. 6, to better fit the elastic tensile forces to the side contours of the pants layer. It is naturally also possible to consider forming large apertures in more or other areas than shown in the elastic net in FIG. 6. For a more detailed description of how one can stretch and configure elastic materials, such as elastic nets for elastifying a pants layer, reference is made to our Swedish patent application with application number SE 9500387-7 filed on the same day as the present application.

Elastic films and fiber cloth can be stretched and configured in principle in the same way as the elastic net in FIG. 6. To make parts of them better follow the side edges of the crotch part, holds or slits can be made in suitable places, for example in places corresponding to the large apertures 22,23 in the net shown in FIG. 6.

Elastic threads, ribbons or similar can be applied in a different way, which is described more closely in our Swedish patent application with application number SE 9500384-4, which was also filed on the same day as the present patent application. In this case the laying-out pattern for the elastic threads have been adapted to the contours of the side edges of the crotch part. Elastic nets, films or fiber cloth show, however, in comparison with threads, a surface with a distribution which is comparatively large in two mutually perpendicular directions, and fitting to the contours of the side edges of the pants layer can be made through the above mentioned reconfiguring technique, i.e. for example, cutting of threads in the elastic net or slitting of the elastic film or fiber cloth.

In a possible method for manufacturing the pants layer 5, the material layer 21 can be cut out of a running roll of material, from which periodically segments are cut from each side of the roll, in order to form the bent side edges 18,19 in it, which will form the crotch part 11 of the pants layer when individual material layers 21 are cut from the roll. Elastic means 20 can for example be applied over the complete roll after the periodically repeated bent side edges have been cut out, but it could instead be applied over the complete roll before the periodically repeated bent side edges have been cut out. In order to adjust the pants layer 5 to a special shape and size, alternatively a certain part of the pants layer can be removed, for example in connection with the cutting of the leg openings. This means that even a part of the elastic means 20 can be removed in connection with this operation. In other words, it is not necessary that elastic means 20 are always arranged inside the side edges 14–19 of the material layer, e.g. in crotch part 11, such as shown in FIG. 6, before the leg openings are cut out.

In order to finally complete pants layer 5 as it is shown in FIG. 6, respectively joined together during use in FIG. 1, pants layer 5 comprises an additional essentially inelastic material layer 21. In this way the elastic net 20 in a prestressed state is placed between two essentially inelastic material layers 21, see FIG. 7. These can preferably be of the same type in order to facilitate joining them together, for example by ultrasonic welding, but is naturally also possible that they can be of different types. The joining together can also be achieved by means of other means, e.g. glue. This implies that the second material layer is appropriately cut out in the same way as the first, preferably simultaneously with it, after both material layer paths run together with the elastic means between them.

Because material layers 21 are inelastic and therefore cannot be stretched in any direction to a noticeable degree, by joining the elastic net 20 between the inelastic material layers 21, the direction and the magnitude that the elastic means 20 can stretch out the pants layer 5 has been fixed. Elastic net 20 is preferably not directly connected with either of the material layers, but is instead indirectly fastened through the material layers 21 being joined to each other in the region in several of the net apertures. In this way, net 20 is fixed fast between the material layers 21.

In this way the front respectively rear waist parts 9 respectively 10 will have elastic forces which in the main work in the circumferential direction of the pants waist opening 2 (see FIG. 1), and the crotch part 11 will have elastic forces which in the main work in the circumferential direction of the pants leg openings 3,4. Elastic forces in the pants waist parts 9,10 perpendicular to the circumferential direction of the pants waist opening 2, which would have significance for the functioning of the pants will hereby not occur.

Another reason for limiting the possibility of stretching for the elastic means is that it should not be overloaded. At the maximum stretch length, which is determined during the placement on the inelastic material layers, forces on the pants layer will continue to be taken up by the inelastic material layers, which are relatively unstretchable and which set a limit to further stretching of the elastic means.

It is not necessary for the pants layer to be made of a laminate comprising two essentially inelastic and unstretchable material layers with an intermediate elastic means. The material layers can in themselves comprise more than one layer and it is conceivable to leave out one material layer completely. In this latter case the elastic means must be attached to one side of the remaining single material layer. This can, for example, be done in the way shown in our Swedish patent application SE-9304232-3. This method is characterized in that the elastic material, e.g. an elastic net or an elastic thread, comprises at least one elastic component and at least one thermoplastic component and that only the thermoplastic component, or components, are joined with the material layer. For more details reference is made to said application.

The absorbent pants 1 in FIG. 1 also comprises an outer barrier layer 6. The outer barrier layer 6 can, for example, be made of a liquid impermeable film, e.g. a polyethylene film, or of a fiber cloth (nonwoven) which is made liquid-impermeable or of a laminate or an extrusion laminate of a liquid-impermeable film and a fiber cloth. In the last example, the fiber cloth is appropriately placed outermost when seen from the pants layer 5, with the intention of giving the pants a soft and less plastic-like appearance, and an outer layer which at the same time feels comfortable to put on. The outer barrier layer can further be made of a stretchable material.

Figure 8:
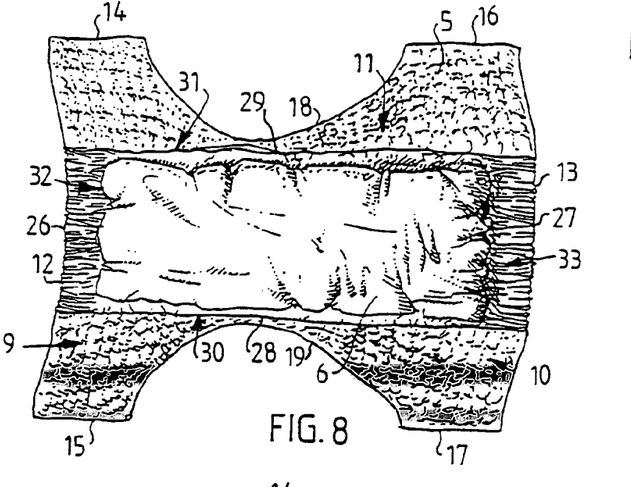
FIG. 8 shows schematically a plan view, and in the stretched condition, of the pants layer according to FIG. 7 and according to the first embodiment of the invention, seen from the barrier layer side.

FIG. 8 (which shows the opposite side of the pants layer 5 from FIG. 7) shows pants layer 5 in a flat and unassembled condition with the outer barrier layer 6 placed on pants layer 5. Pants layer 5 is placed prestressed on the outer barrier layer 6. Outer barrier layer 6 has end and side edges 26,27 respectively 28,29. End edges 26,27 are joined with the pants layer 5 at the parts 32,33 of it which extend from the respective end edges 12,13 of the pants layer 5, and with a short piece directed in towards the crotch part 11. Side edges 28,29 are joined with the pants layer 5 in the regions 30,31 between the respective side edges 14–17 which in the assembled condition form the respective side seams 8, see FIG. 1, and the imaginary longitudinal line of symmetry. In this manner, the outer barrier layer 6 will be essentially unloaded by tensile forces in the pants layer 5, which are perpendicular to the longitudinal line of symmetry in a region which is limited by the joining regions 30–33 between the end and side edges 26–29 of the outer barrier layer 6 with the pants layer 5. In this way, pants layer 5 is able to draw together and stretch out without being influenced by forces from the outer barrier layer 6, and is in this way able to lie against the body over essentially all its surface without any play needing to form between the pants layer 5 and the body of the user. In this way, the outer barrier layer 6 has been disengaged from the pants load-bearing inner layer, i.e. pants layer 5, and all transverse forces, i.e. forces in the circumferential direction of the waist opening 2 (see FIG. 1), will be essentially taken up by pants layer 5 alone.

An advantageous embodiment will now be described with reference to FIGS. 3–7. Pants layer 5 is equipped with one or more openings for the passage of urine and/or faeces. The openings are shown in the Figures as holes, but other types of openings which allow the passage of urine respectively faeces are naturally conceivable, e.g. slits or perforated parts of the pants layer, i.e. parts having a large number of very small holes. The last mentioned variation is, however, less suited for the passage of faeces, but is best suited for the passage of urine. It has been shown earlier in FIG. 6 that it is possible to achieve large apertures 22,23 in the elastic net 20 to fit this to the contours of the side edges of the pants layer in the crotch part 11. In the finished pants layer 5 shown in FIG. 7 there are two openings 34,35 which have positions corresponding with the position of the large apertures 22,23 in FIG. 6. Apertures 22,23 have therefore a double role to play. As well as contributing to the reshaping of the placing and positioning of the elastic threads in net 20, they can also be used as appropriate areas of the pants layer 5 to receive the openings 34,35, which shall permit the passage of urine respectively faeces. The smaller opening 34 has six sides and is arranged in the front part 24 of crotch part 11. The somewhat larger opening 35 is triangular and arranged in the rear part 25 of crotch part 11.

Instead of forming in advance large apertures in the elastic net which have a position which corresponds to the areas in the pants layer in which the openings shall be made, it is naturally possible that the large apertures are formed at the same time as the opening after the elastic net has been joined to the inelastic material layer, i.e. the openings are formed in the completed pants layer which comprises material layers on one or both sides of the elastic net.

The size and the positioning of the two openings, which are shown in FIG. 7, can naturally vary with reference to the size and anatomy of the user category which the pants, in which the pants layer is included, is intended to fit.

Figure 4:
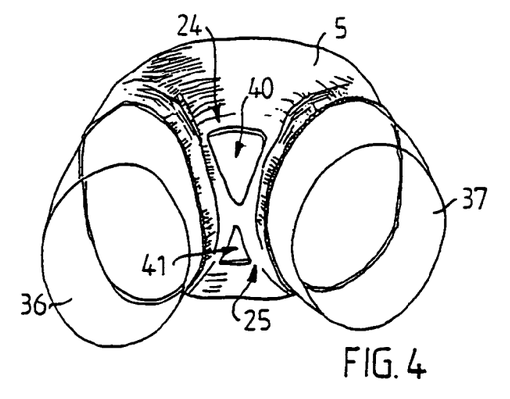
FIG. 4 shows a perspective view from below of the load-bearing pants layer of an absorbent pants applied to a transparent doll simulating a user, according to a third embodiment of the invention and with other parts of the pants removed.
Figure 5:
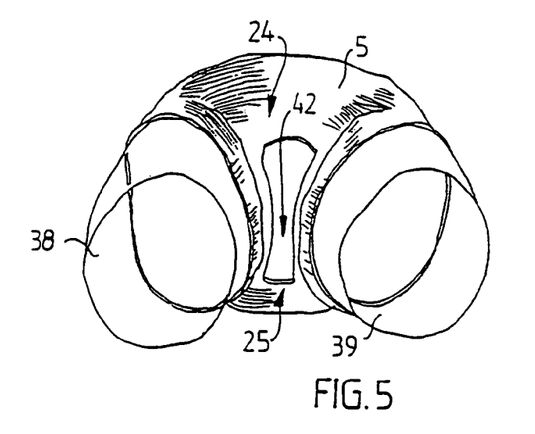
FIG. 5 shows in the same way as in FIG. 4 a perspective view from below of the load-bearing pants layer of an absorbent pants according to a fourth embodiment of the invention and with other parts of the pants removed.

FIGS. 4 and 5 show two different variations of the openings in pants layer 5. The pants are shown precisely like in FIG. 3, with the outer barrier layer and the absorption body removed. The pants are shown from beneath, i.e. the observer sees the pants in the direction from the feet of the user and upwards towards the crotch of the user. The pants are further shown fitted on a transparent doll-which simulates how the pants are envisaged sitting on a living user. The truncated legs of the doll have been given reference numerals 3637 respectively 38,39. FIG. 4 shows two openings, precisely as in the pants layer of FIG. 7, but of somewhat different size and shape to the openings in FIG. 7. The front opening 40 in the front part 24 of crotch part 11 is triangular and bigger than the rear opening 41 in the rear part 25 of crotch part 11. The rear opening 41 is also triangular.

FIG. 5 shows a variation with only one single opening 42. This single opening is relatively much longer than any of the other described openings, in order to serve as an opening for the passage of urine as well as faeces. The somewhat wider end of opening 42 is arranged in the front part of crotch part 11, and the somewhat narrow end of opening 42 is arranged in the rear part of crotch part 11.

FIG. 3 shows in perspective the front part of opening 34 in the front part 24 of crotch part 11 of the pants layer. However, opening 34 in FIG. 3 could also illustrate the front part of the single elongate opening 42 in FIG. 5, or the front part of the front opening 40 in FIG. 4. It should be noted that the shape and size of the openings will change when the pants layer 5 is subjected to forces, for example, depending on how tightly pants layer 5 fits around the body of the user.

As described earlier, the outer barrier layer 6 is fastened to pants layer 5, see e.g. FIGS. 1 and 8. The barrier layer 6 is in this way arranged at the same level as openings 34,35, see FIGS. 7 and 8, which each show a side of pants layer 5, and the outer barrier layer 6 is joined with pants layer 5 in the regions 30–33 around the openings 34,35.

As mentioned earlier, pants layer 5 has an opening in the shape of a hole in the front region 24 of crotch part 11, seen in the direction towards the front waist part 9, and an opening 35, also in the shape of a hole, arranged in a rear region 25 of crotch part 11, seen in the direction towards the rear waist part 10. These two openings 34,35 are intended for the passage of urine respectively faeces through pants layer 5 to not shown front respectively rear pockets between pants layer 5 and the outer barrier layer 6, which pockets will be expounded on below.

One or more absorption bodies 7 are arranged between pants layer 5 and the outer barrier layer 6. These can comprise any sort or sorts of known absorption material, for example cellulose pulp fluff, superabsorbent polymers (by this is meant polymers with a capacity to absorb many times their own weight of fluids), for example cross-connected polyacrylates, absorbent foam or mixtures of these. The absorption bodies are preferably covered with a liquid-permeable covering material, but this is not absolutely necessary. If a liquid-permeable covering material is used, it can for example be made of a fiber cloth (nonwoven), for example of the type thermobond or spunbond and, for example, comprising polypropylene fibers.

An example of an absorption body and water-permeable covering layer is shown in detail in FIGS. 10–13 and is described in detail below.

Figure 14:
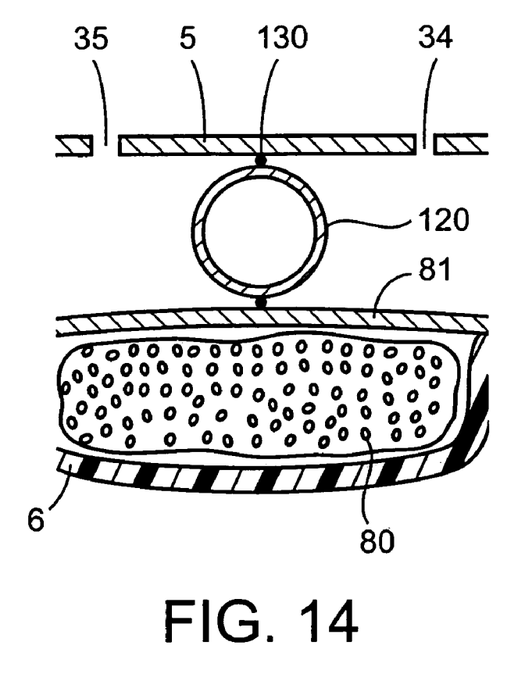
FIG. 14 shows a partial cross sectional view of an absorbent pants having a liquid barrier which is arranged between the pants layer and the liquid permeable covering layer in a region between the front opening and the rear opening.

The pockets are separated from each other so that the transfer of urine and faeces between pockets is prevented. Various examples of pockets separated from each other are shown in detail in FIGS. 14–16 and are described below. For example, a fluid barrier 120 in the shape of a pipe body or a tube body can be placed between pants layer 5 and the absorption body, as shown in FIG. 14. This fluid barrier 120 extends transversely between the fastenings 30,31 of the pants layer 5 in the side edges 28,29 of the outer barrier layer 6 in a region between both openings 34,35. The upper and underside of the fluid barrier 120 are fastened to pants layer 5 and to the water-permeable covering layer 81 above the absorption layer 80, by means of a joint 130 with a slight extension in the pants layer's 5 longitudinal direction, e.g. by means of a string of glue. The fluid barrier 120 can be made, for example, from a polyethylene film which is made in the shape of a tube. Instead of a tube body, which has two walls, a single-wall barrier, e.g. a bellows-folded polyethylene film, can in a corresponding manner be arranged between the pants layer 5 and the liquid-permeable covering layer 81. For more details concerning suitable shaping of such liquid barriers, reference is made to our Swedish patent application SE-9400916-4.

The liquid barrier shall, however, exactly as for the outer barrier layer 6, be fastened in pants layer 5 so that, in the same region as the outer barrier layer 6, it is essentially not loaded by tensile forces in pants layer 5 which act in a direction perpendicular to the longitudinal line of symmetry.

Figure 15:
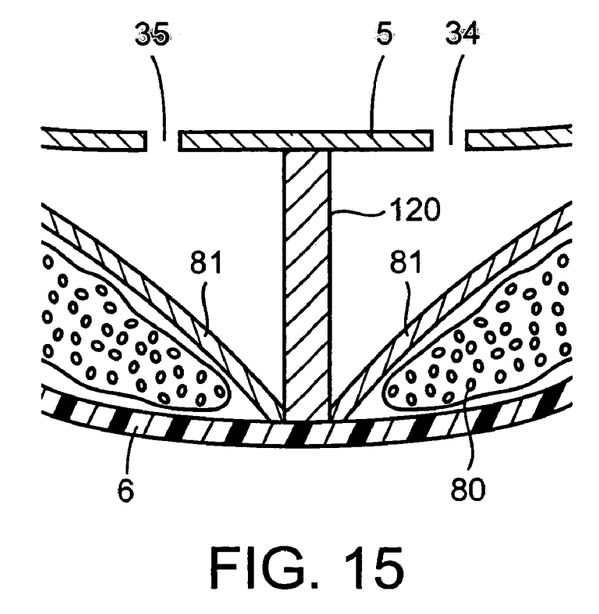
FIG. 15 shows a partial cross sectional view of the absorbent pants showing a liquid barrier.
Figure 16:
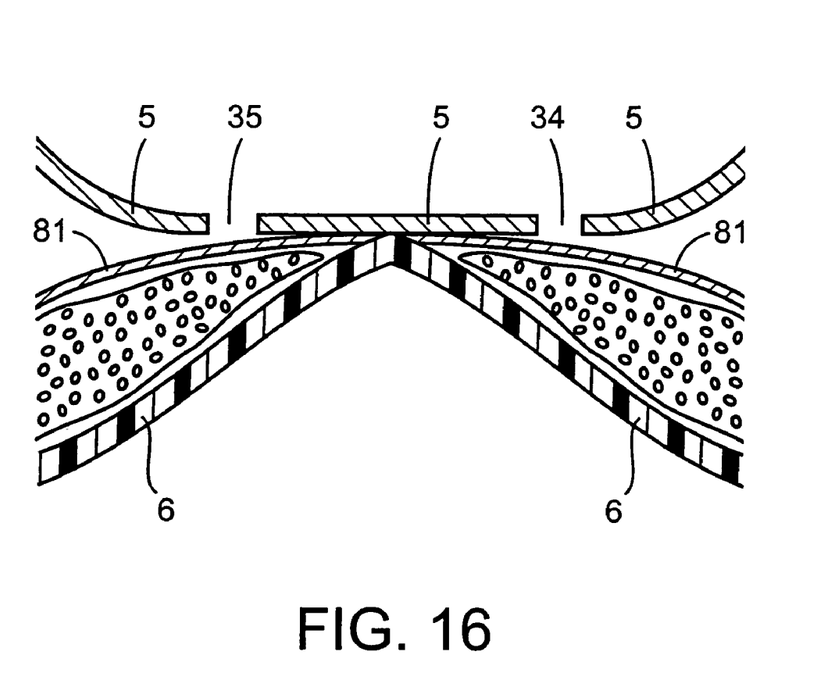
FIG. 16 shows a partial cross sectional view of a part of the pants layer between the front opening and the rear opening which is joined with a part of the outer barrier layer which extends from a side edge of the outer barrier layer to the other side edge.

In this example, the absorption body extends with parts on both sides of the fluid barrier, and this separates the pockets from each other in the empty space between the pants layer 5 and the water-permeable covering layer of the absorption body. This is, however, sufficient to prevent faeces from spreading from the back pocket to the front. In a variation, two separate absorption bodies are arranged with one in each pocket and the liquid barrier 120 is placed between the pants layer 5 and the outer barrier layer 6, as shown in FIG. 15. FIG. 16 shows another embodiment, wherein a part of the pants layer 5 between the front opening and rear opening is joined with a part of the outer barrier layer 6 which extends from one side edge of the barrier layer 6 to the other side edge.

Yet another variation has only one absorption body arranged in the front pocket and nothing at all in the back one, in which only faeces are intended to be collected. Possibly an absorption body with a reduced absorption capacity can be arranged in the back pocket, in order to absorb the loose fractions of the faeces. It is also conceivable to have no absorption body at all in the traditional sense inside the pocket or pockets, but instead to coat the interior of the outer barrier layer with an absorbent material, of which the absorption capacity is adapted for the absorption purpose. For example, a high bulk fiber cloth with hydrophilic properties can be laminated or in some other way joined to the interior of the outer barrier layer, i.e. on the inside of the pocket, or at least one of the pockets.

Figure 2:
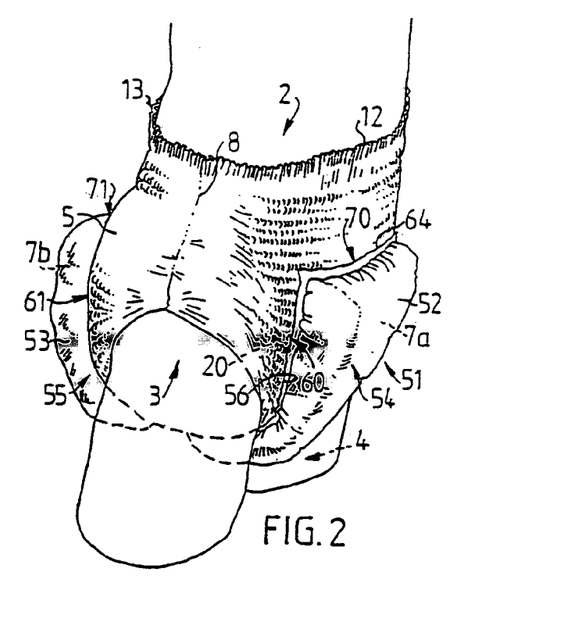
FIG. 2 shows a perspective view seen from the side of an absorbent pants according to a second embodiment of the invention as shown on a schematically indicated user.
Figure 9:
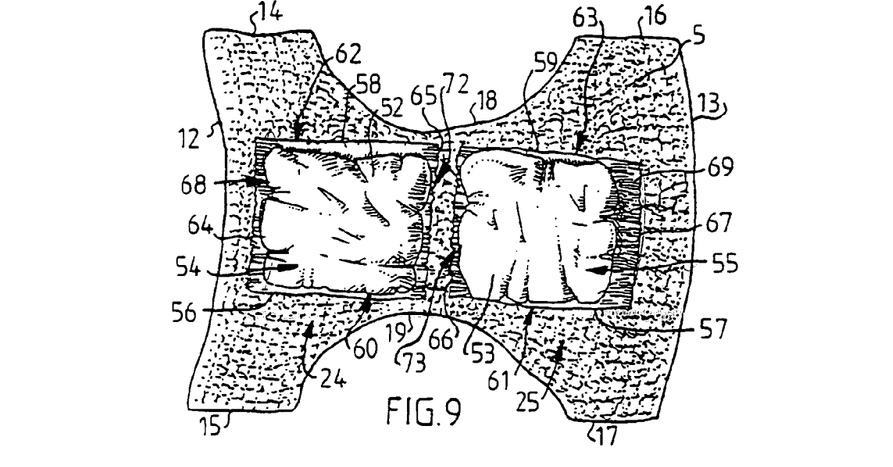
FIG. 9 shows schematically a plan view, and in the stretched condition, of the pants layer according to FIG. 7 and according to the second embodiment of the invention, seen from the barrier layer side.

With reference to FIGS. 2, 7 and 9, a further embodiment of the pants according to the invention shall be described.

These pants 51 are identical with pants 1 according to FIG. 1, with the exception of the shaping of the outer barrier layer. FIG. 9 shows for this embodiment the corresponding sides of pants layer 5 in FIG. 7. Pants 51 has two separate barrier layers 52,53. A front barrier layer 52 is joined with the pants layer 5 surrounding opening 34 in the front part 24 of crotch part 11, and a rear barrier layer 53 is joined with the pants layer 5 surrounding opening 35 in the rear part 25 of crotch part 11. The space between pants layer 5 and the respective front and rear barrier layers 52,53 form a front pocket 54 respectively a rear pocket 55, see e.g. FIG. 2. These pockets are separated from each other in that the front respectively rear barrier layers 52,53 do not overlap each other but are spaced apart in the longitudinal direction of the pants layer.

An absorption body 7a is placed in the front pocket 54 and an absorption body 7b is placed in the rear pocket 55, see FIG. 2. These absorption bodies can be made as described above.

In the same way as described for the earlier embodiments, the front respectively rear barrier layers 52,53 are connected to a pre-tensioned pants layer 5. The respective side edges 56–59 of the barrier layers 52,53 are joined with the pants layer 5 in the regions 60–63 between the respective side seam 8 and the imaginary longitudinal line of symmetry of the pants layer 5. Barrier layers 52,53 according to the embodiment shown in FIGS. 2 and 9 each have two end edges 64,65 respectively 66,67. The respective end edges 64 respectively 67, which lie nearest the respective end edges 12 respectively 13 of the pants layer, are in FIG. 9 joined to parts 68,69 of the pants layer 5, a bit before its respective end edges 12,13. In FIG. 2, the joining parts 70,71 are arranged a bit further in, reckoned from the respective end edges 12,13 of the pants layer. In this connection it can be noted that the respective end edges 64,67 of the front 52 and the rear 53 barrier layer could instead be fastened to parts of the end edges 12,13 of the pants layer in the same way as in the embodiment according to FIG. 1 and vice versa. The end edges 65,66 lying nearest to each other of the respective front and rear barrier layers 52,53 are joined with pants layer 5 within the regions 72,73 within a central region of crotch part 11. In this way, the respective front and rear barrier layers 52,53 are joined around the respective openings 34,35 in pants layer 5.

Figure 10:
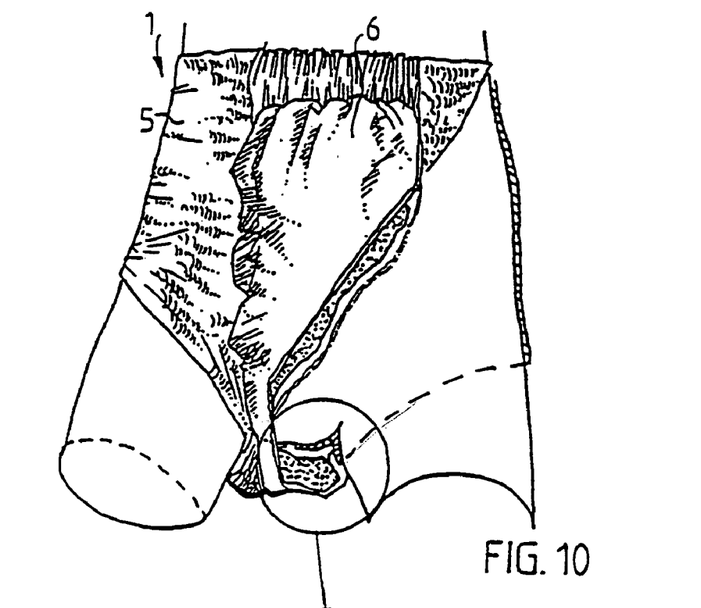
FIG. 10 shows schematically a perspective view from in front and partially in section of a fifth embodiment of the invention and how this is supposed to function.
Figure 10A:
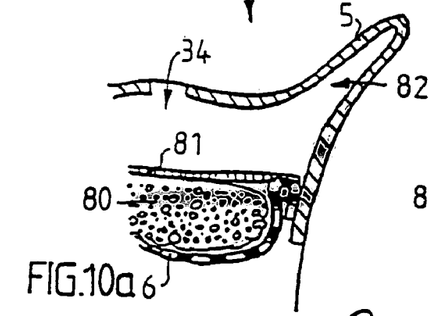
FIG. 10a shows an enlargement of the area ringed in FIG. 10.
Figure 10B:
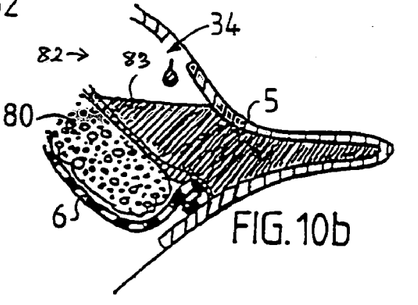
FIG. 10b shows the same region shown in FIG. 10a but at a 45° angle.
Figure 10C:
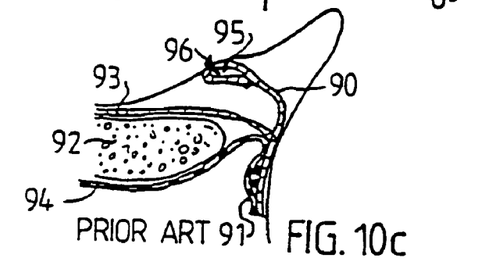
FIG. 10c shows schematically the corresponding area which is ringed in FIG. 10, but for a known diaper with raised barrier flap.

With reference to FIGS. 10 to 10c, it shall be described how an embodiment of the pants according to the invention is supposed to function.

FIG. 10 shows an absorbent pants of the same sort as in FIG. 1. The pants 1 are seen from in front in the envisaged position of use on a user indicated by solid and dashed lines. A part of the pants is shown in section and another part of it is circled and shown enlarged in FIG. 10a.

FIGS. 10 and 10a show how pants layer 5 lies closely against the body of the user and continues up into the groin. Pants layer 5 is shown broken at opening 34. FIG. 10a also shows an absorption body 80, the outer barrier layer 6 and a liquid-permeable covering layer 81 placed on the side of the absorption body 80 which is facing towards pants layer 5. Between the pants layer 5 and the liquid-permeable layer 81 a pocket 82 is formed. Examples of all these elements have been mentioned above and will not be repeated again here.

FIG. 10b shows how urine 83 has come into pocket 82 through opening 34 and has not yet been able to pass through the liquid-permeable covering layer 81 and be absorbed by absorption body 80. This is not an unusual situation because absorbent pants often slope when the user lies to one side or is inclined in one way or another. In the position shown, the absorbent body 80 has therefore not been able to suck in the liquid in the way intended, but instead it has accumulated in the completely enclosed corner of pocket 82. It is not at all possible for anything to leak out because pants layer 5 is hydrophobic and the outer barrier 6 is liquid-impermeable. Because the pants layer 5 clings elastically to the skin of the user over essentially its whole surface and, as mentioned earlier, essentially cannot be influenced by forces from the absorption body or the outer barrier layer, it will neither lose contact with the body of the user nor move from its position against the user, neither in transverse nor in longitudinal direction, in the regions, so important for the prevention of leakage, around the opening 34 (or the openings if there are several). If opening 34 is correctly dimensioned and correctly placed in relation to the ureathral opening of the user, essentially all the urine emitted will be caught in pocket 82, from which it then cannot leak out, but can only be absorbed by absorption body 80. If, contrary to expectation, some liquid should come in between pants layer 5 and the skin of the user along the sides of opening 34, this liquid will have a relatively long way to run before it can leak out over the edges of pants layer 5.

As a comparison with the present invention, FIG. 10c shows an example of a known raised leakage barrier 90 for a diaper. The known leakage barrier 90 is made of a separate piece of material placed on the elastic leg cuff 91. The diaper comprises as usual an absorption body 92, a liquid-permeable covering layer 93 and an outer barrier layer 94. Leakage barrier 90 comprises an elastic means 95 with the help of which it can be raised up from the liquid-permeable covering layer 93.

The outer barrier layer 94 forms the pants-forming layer of the assembled diaper and is therefore the layer which bears the loads of the diaper. In this way the outer barrier layer can move in relation to the user in step with the forces which influence it. Because the leakage barriers are joined with the outer layer, they can therefore also move in relation to the user. Leakage barrier 90 can therefore be forced to lose its contact with the user or be moved in the transverse or longitudinal direction out of its intended position on the user. Since leakage barrier 90 only has a very narrow contact line with the user, fluid will very quickly be able to pass the leakage barrier as soon as it loses contact with the user. After this, there only remains the sealing leg cuff 91 as the final barrier to leakage. Because even this is subjected to forces from the outer barrier layer, there is a large risk that even this will not stay sealed. In any case the largest damage has already taken place when fluid has come past the leakage barrier 90. In this case, liquid will come into contact with the skin of the user in the region outside the leakage barrier 90 and inside the elastic leg cuff 91. This fluid will cause skin irritation, which naturally causes the user discomfort.

It should be noted that if free liquid, which collects in the space between leakage barrier 90 and liquid-permeable covering layer 93, accumulates against leakage barrier 90 when the diaper slopes in the same way as shown in FIG. 10b, then the pressure on leakage barrier 90 will increase to an even higher degree, and therefore also the risk for leakage.

Figure 11:
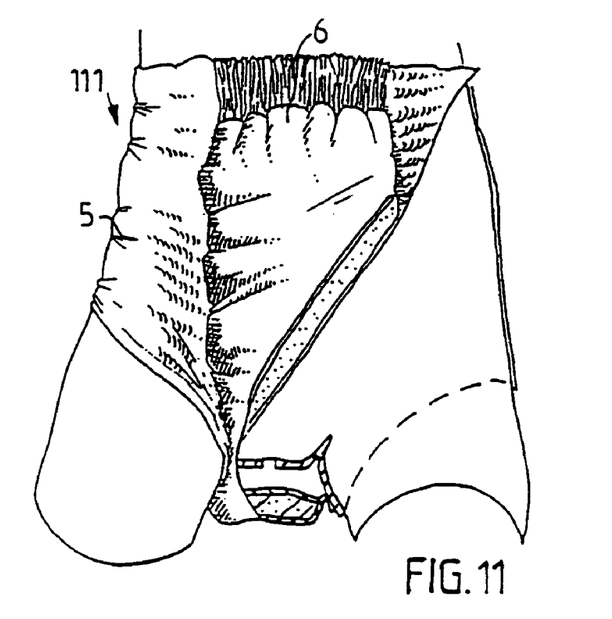
FIG. 11 shows schematically a perspective view from in front and partially in section of a sixth embodiment of the invention and how this is intended to function.
Figure 12:
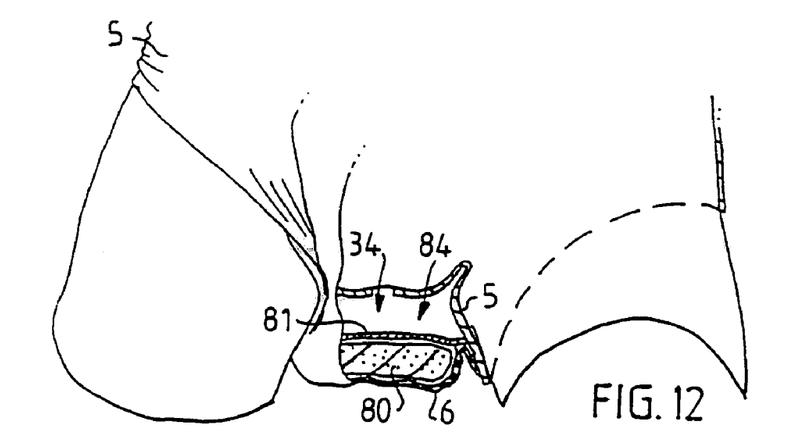
FIG. 12 shows an enlargement of FIG. 11.

FIG. 11 shows in a view similar to that in FIG. 10 an absorbent pants 111 according to yet another embodiment of the invention. FIG. 12 shows an enlargement of a part between the legs of the user of the pants in FIG. 11. The difference between the pants according to FIG. 10 is that an even larger distance between pants layer 5 and the absorption body 10 has been made, compared with the pants in FIG. 10. In this way a deeper pocket 84 is obtained.

Figure 13:
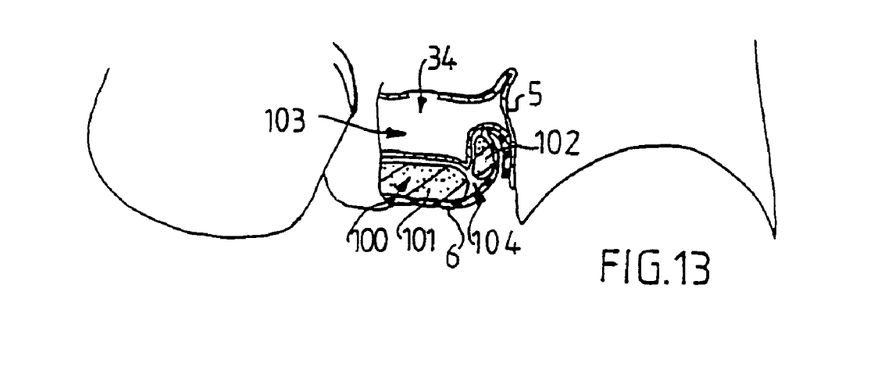
FIG. 13 shows an enlargement of FIG. 11, but for a seventh embodiment of the invention.

FIG. 13 shows a similar enlargement to FIG. 12, but shows an alternative absorption body 100, which comprises a larger main body 101, centrally arranged between two smaller side bodies, of which only one 102 is shown in the Figure. Side bodies 102 can swing up around the hinge which is formed in split 104 between the respective side body 102 and main body 101. In this way, a pocket 103 with an even greater depth than for the earlier shown examples but with a retained amount of absorption capacity, compared with a single assembled absorption body comprising exactly the same absorption material, is achieved. The construction of absorption body 100 is described in more detail in our Swedish patent application SE-9304131-7, to which reference is hereby made. Absorption body 100 with a main body and side bodies can naturally advantageously also be used in the earlier shown embodiments.

The invention has been described as a pants for the absorption or urine. Such pants are often called pant diapers. Known pant diapers have side seams closed by the manufacturer, and possibly provided with the possibility of being opened. The invention, however, concerns also such pant diapers which can be opened and reclosed, and such which can be delivered by the manufacturer in the open condition and which are supplied with fastening means which are intended to be fastened together by the user in a way directed by the manufacturer, in order to thereafter be put on the user in the assembled pants configuration. An example of such a pant diaper has been given earlier in this description. The invention is furthermore also adaptable for so-called sanitary pants, i.e. pants specially intended to absorb menstruation fluids.

As shown above, many modifications are possible within the scope of the invention, and it should therefore only be considered limited according to the following claims.

What is claimed is:

1. An absorbent pants comprising:
   a hydrophobic pants layer which during use of the pants faces a body of a user, the pants layer being assembled to itself or being able to be assembled to itself so that the pants layer by itself defines a waist opening and two leg openings, said absorbent pants arranged such that only the pants layer of the absorbent pants is in contact with the user when the absorbent pants are being worn;
   an outer barrier layer which is impermeable and arranged outside of the pants layer relative to the body of the user during use of the pants and is fastened to the pants layer, the pants layer has a surface area which is greater than a surface area of the outer barrier layer;
   at least one absorption body arranged between the pants layer and the outer barrier layer;
   a liquid-permeable covering layer arranged on the absorption body between the absorption body and the pants layer, the absorption body being arranged between the liquid-permeable covering layer and the outer barrier layer;
   the liquid-permeable covering layer extending laterally beyond the absorption body and portions of the liquid-permeable covering layer that extend laterally beyond the absorption body being directly and permanently affixed to the outer barrier layer to laterally surround the absorption body;
   the pants layer, the outer barrier layer, and the liquid-permeable covering layer arranged so as to define a space in the form of a pocket between the pants layer and the liquid-permeable covering layer; and
   at least one opening in the pants layer, said opening arranged over the pocket for passage of at least one of urine and faeces into the pocket.

2. The absorbent pants according to claim 1, wherein the pants layer comprises a front and a rear waist part, which during use of the pants are intended to together surround the stomach and backside parts, respectively, of the user, and a crotch part between the front and rear waist parts, which during use of the pants is intended to be arranged between the legs of the user, the front and rear waist parts each have an end edge and two side edges and the crotch part has two side edges, further the side edges of the respective front and rear waist parts on the same side of an imaginary longitudinal line of symmetry, drawn from the end edge of the front waist part to the end edge of the rear waist part, are joined with each other to form a side seam, by which the respective end edges of the front and rear waist parts form the waist opening of the pants, and the side edges of the crotch part form the respective leg openings of the pants, and the side seams extend between the waist opening and respective leg openings.

3. The absorbent pants according to claim 2, wherein the pocket is a front pocket and the absorbent pants further comprises a rear pocket adjacent the front pocket and between the pants layer and the outer barrier layer, and wherein the at least one opening is a front opening arranged in a front region of the crotch part for the passage of urine through the pants layer to the front pocket, the absorbent pants further comprising a rear opening arranged in a rear region of the crotch part for the passage of faeces through the pants layer to the rear pocket, the pockets are separated from each other so that the transfer of urine and faeces between the pockets is prevented.

4. The absorbent pants according to claim 3, wherein a liquid barrier is arranged between the pants layer and the outer barrier layer in a region between the front opening and the rear opening and between the rear and front pockets in the form of at least one liquid-impermeable layer, connected to the pants layer and the outer barrier layer to separate the pockets.

5. The absorbent pants according to claim 4, wherein the at least one liquid-permeable layer is polyethylene.

6. The absorbent pants according to claim 3, wherein a liquid barrier is arranged between the pants layer and the absorption body in a region between the front opening and the rear opening and between the rear and front pockets, in the form of at least one liquid-impermeable layer, connected with the pants layer and the liquid-permeable covering layer to separate the pockets.

7. The absorbent pants according to claim 6, wherein the at least one liquid-impermeable layer is polyethylene.

8. The absorbent pants according to claim 3, wherein a part of the pants layer between the front opening and the rear opening is joined with a part of the outer barrier layer which extends from one side edge of the outer barrier layer to the other side edge to separate the pockets.

9. The absorbent pants according to claim 3, wherein the outer barrier layer comprises at least two separate layers of which a front barrier layer is joined with the pants layer surrounding the opening in the front part of the crotch part to define the front pocket, and a rear barrier layer is joined with the pants layer surrounding the opening in the rear part of the crotch part to define the rear pocket.

10. The absorbent pants according to claim 1, wherein the pants layer is elastic.

11. The absorbent pants according to claim 1, wherein the pants layer comprises elastic and at least one essentially inelastic material layer, and that the elastic is placed pretensioned on the essentially inelastic material layer or layers.

12. The absorbent pants according to claim 11, wherein the essentially inelastic material layer is essentially unstretchable.

13. The absorbent pants according to claim 12, further comprising a second inelastic material layer and wherein the elastic is placed pretensioned between the two inelastic material layers.

14. The absorbent pants according to claim 11, wherein the elastic is placed pretensioned in the transverse direction in front and rear waist parts of the pants layer and placed pretensioned in the longitudinal direction in a crotch part of the pants layer, whereby the front and rear waist parts have elastic forces which in main work in the circumferential direction of the waist opening of the pants, and the crotch part has elastic forces which in main work in the circumferential direction of the leg openings of the pants.

15. The absorbent pants according to claim 14, wherein the outer barrier layer has end and side edges of which the side edges are joined with the pants layer in first and second joining regions between respective side seams joining the front waist part and the rear waist part and an imaginary longitudinal line of symmetry, so that the outer barrier layer is not loaded by tensile forces perpendicular to the imaginary longitudinal line of symmetry between said first and second joining regions and between joining regions of the end edges of the outer barrier layer with the pants layer.

16. The absorbent pants according to claim 15, wherein said joining regions of the end edges of the outer barrier layer are arranged inside end edges of respective front and rear waist parts.

17. The absorbent pants according to claim 4, wherein the elastic is made of an elastic net, an elastic film, an elastic cloth or of several elastic threads or tapes.

18. The absorbent pants according to claim 11, wherein the essentially inelastic material layer is made of a fiber nonwoven cloth material.

19. The absorbent pants according to claim 18, wherein the fiber cloth material is one of meltblown, spunbound, and thermobond.

20. The absorbent pants according to claim 19, wherein the fiber cloth material is polypropylene.

21. The absorbent pants according to claim 11, wherein the elastic has a stretch of at least 25%.

22. The absorbent pants according to claim 1, wherein the pants layer is joined pretensioned with the outer barrier layer.

23. The absorbent pants according to claim 1, wherein a connection area between the outer barrier layer and the pants layer extends around the at least one opening.

24. The absorbent pants according to claim 1, wherein the outer barrier layer is made of a liquid-impermeable film, a fiber cloth which is made liquid-impermeable or a laminate or extrusion laminate of a liquid-impermeable film and a fiber cloth, with the fiber cloth placed outermost when seen from the pants layer.

25. The absorbent pants according to claim 1, wherein the pants are a pant diaper.

* * * * *